US012578112B2

(12) United States Patent
Kubota et al.

(10) Patent No.: US 12,578,112 B2
(45) Date of Patent: Mar. 17, 2026

(54) DISPLAY SYSTEM, DISPLAY METHOD, AND PROGRAM

(71) Applicant: Panasonic Intellectual Property Management Co., Ltd., Osaka (JP)

(72) Inventors: Hirofumi Kubota, Osaka (JP); Fei Liu, Osaka (JP); Noriaki Fukumoto, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 302 days.

(21) Appl. No.: 18/256,859

(22) PCT Filed: Oct. 8, 2021

(86) PCT No.: PCT/JP2021/037411
§ 371 (c)(1),
(2) Date: Jun. 9, 2023

(87) PCT Pub. No.: WO2022/137735
PCT Pub. Date: Jun. 30, 2022

(65) Prior Publication Data
US 2024/0027088 A1 Jan. 25, 2024

(30) Foreign Application Priority Data

Dec. 25, 2020 (JP) ................................. 2020-217935

(51) Int. Cl.
*F24F 11/52* (2018.01)
*G01K 1/024* (2021.01)
(Continued)

(52) U.S. Cl.
CPC .............. *F24F 11/52* (2018.01); *G01K 1/024* (2013.01); *G01K 1/14* (2013.01); *G01N 33/0027* (2013.01); *G01K 2201/00* (2013.01)

(58) Field of Classification Search
CPC ............ F24F 11/52; F24F 11/63; F24F 11/79; F24F 2110/10; F24F 2110/20; G01K 1/024;
(Continued)

(56) References Cited

U.S. PATENT DOCUMENTS 9,243,811 B2 1/2016 Saito et al.
2017/0153032 A1 6/2017 Ashgriz et al.
(Continued)

FOREIGN PATENT DOCUMENTS

CN 103994556 A 8/2014
CN 107480457 A 12/2017
(Continued)

OTHER PUBLICATIONS

English Translation of "JP-2004060978-A" (Year: 2004).*
(Continued)

*Primary Examiner* — Charles R Kasenge
(74) *Attorney, Agent, or Firm* — Rimon P.C.

(57) ABSTRACT

A display system includes an acquirer, an estimator, and a controller. The acquirer acquires a first detection value and a second detection value from a temperature sensor and a humidity sensor, respectively. The temperature sensor and the humidity sensor are both included in a ventilator that ventilates a room. The estimator estimates, based on the first detection value and the second detection value that are acquired by the acquirer, a predicted mean vote distribution representing a distribution of predicted mean votes in a height direction in the room. The controller makes a display device present the predicted mean vote distribution estimated by the estimator.

12 Claims, 5 Drawing Sheets

(51) Int. Cl.
 *G01K 1/14* (2021.01)
 *G01N 33/00* (2006.01)

(58) Field of Classification Search
 CPC ................ G01K 1/14; G01K 2201/00; G01N
 33/0027
 See application file for complete search history.

(56) References Cited

U.S. PATENT DOCUMENTS

| | | |
|---|---|---|
| 2018/0187910 A1 | 7/2018 | Kusukame et al. |
| 2018/0293038 A1 | 10/2018 | Meruva et al. |
| 2021/0011443 A1 | 1/2021 | Mcnamara et al. |
| 2022/0333809 A1 | 10/2022 | Higuchi et al. |

FOREIGN PATENT DOCUMENTS

| | | | |
|---|---|---|---|
| CN | 210376401 U | * | 4/2020 |
| CN | 111314800 A | | 6/2020 |
| EP | 3569939 A1 | | 11/2019 |
| GB | 2513945 A | | 11/2014 |
| JP | 2004060978 A | * | 2/2004 |
| JP | 2007-155173 A | | 6/2007 |
| JP | 2007-183032 A | | 7/2007 |
| JP | 2008-075973 A | | 4/2008 |
| JP | 2010-277172 A | | 12/2010 |
| JP | 2012-063055 A | | 3/2012 |
| JP | 6091722 B1 | | 3/2017 |
| JP | 2017-116129 A | | 6/2017 |
| JP | 6678748 B2 | | 4/2020 |
| JP | 2020-134121 A | | 8/2020 |
| JP | 2021-004680 A | | 1/2021 |
| WO | 2018/029757 A1 | | 2/2018 |
| WO | 2020/075244 A1 | | 4/2020 |

OTHER PUBLICATIONS

English Translation of "CN-210376401-U" (Year: 2020).*
International Search Report dated Dec. 21, 2021 issued in International Patent Application No. PCT/JP2021/037411, with English translation.
International Search Report dated Dec. 21, 2021 issued in International Patent Application No. PCT/JP2021/037409, with English translation.
Shinichi Tanabe, "Evaluation of Thermal Comfort in Houses", Housing Research Foundation Annual Report No. 23, pp. 19-32, 1996 with partial English Translation.
P W Li et al., "Application of a weather stress index for alerting the public to stressful weather in Hong Kong", Meteorological Applications, vol. 7, pp. 369-375, 2000.
Office Action and Search Report issued on May 7, 2025 for the corresponding Chinese Patent Application No. 202180084386.7, with the English translation.
Office Action and Search Report issued on May 7, 2025 for the related Chinese Patent Application No. 202180084385.2, with the English translation.
Notice of Reasons for Refusal dated May 21, 2024 issued in the corresponding Japanese Patent Application No. 2022-571077, with English translation.
First Examination Report dated Nov. 21, 2025 issued in the corresponding Indian Patent Application No. 202317039202, with English translation.
Non-Final Office Action dated Nov. 28, 2025 issued in related U.S. Appl. No. 18/256,846.

* cited by examiner

DISPLAY SYSTEM, DISPLAY METHOD, AND PROGRAM

CROSS-REFERENCE OF RELATED APPLICATIONS

This application is the U.S. National Phase under 35 U.S.C. § 371 of International Patent Application No. PCT/JP2021/037411, filed on Oct. 8, 2021, which in turn claims the benefit of Japanese Patent Application No. 2020-217935, filed on Dec. 25, 2020, the entire disclosures of which Applications are incorporated by reference herein.

TECHNICAL FIELD

The present disclosure generally relates to a display system, a display method, and a program, and more particularly relates to a display system including a controller for controlling a display device, a display method, and a program.

BACKGROUND ART

Patent Literature 1 discloses an air conditioner including an infrared sensor for detecting a temperature distribution in a room.

The air conditioner (ventilator) of Patent Literature 1 detects the temperature distribution in the room to evaluate comfortableness for humans. In this case, a predicted mean vote (PMV) is sometimes used as an index to comfortableness. The PMV is measured using, for example, a handy measuring instrument. This limits places and durations for measurement so much that it is difficult to monitor the predicted mean vote all through the year.

CITATION LIST

Patent Literature

Patent Literature 1: JP 6678748 B2

SUMMARY OF INVENTION

In view of the foregoing background, it is therefore an object of the present disclosure to provide a display system, a display method, and a program, all of which are configured or designed to make it easier to monitor the predicted mean vote.

To overcome the problem described above, a display system according to an aspect of the present disclosure includes an acquirer, an estimator, and a controller. The acquirer acquires a first detection value and a second detection value from a temperature sensor and a humidity sensor, respectively. The temperature sensor and the humidity sensor are both included in a ventilator that ventilates a room. The estimator estimates, based on the first detection value and the second detection value that are acquired by the acquirer, a predicted mean vote distribution representing a distribution of predicted mean votes in a height direction in the room. The controller makes a display device present the predicted mean vote distribution estimated by the estimator.

A display method according to another aspect of the present disclosure includes an acquisition step, an estimation step, and a presentation step. The acquisition step includes acquiring a first detection value and a second detection value from a temperature sensor and a humidity sensor, respectively. The temperature sensor and the humidity sensor are both included in a ventilator that ventilates a room. The estimation step includes estimating, based on the first detection value and the second detection value that are acquired in the acquisition step, a predicted mean vote distribution representing a distribution of predicted mean votes in a height direction in the room. The presentation step includes making a display device present the predicted mean vote distribution estimated in the estimation step.

A program according to still another aspect of the present disclosure is designed to cause one or more processors to perform the display method described above.

BRIEF DESCRIPTION OF DRAWINGS

FIG. 4 schematically illustrates an on-screen image displayed on the display device provided for the display system.

DESCRIPTION OF EMBODIMENTS

A preferred embodiment of the present disclosure will now be described in detail with reference to the accompanying drawings. In the following description of embodiments, constituent elements illustrated on multiple drawings and having the same feature will be designated by the same reference sign and description thereof will be omitted herein to avoid redundancy. Note that the embodiment to be described below is only an exemplary one of various embodiments of the present disclosure and should not be construed as limiting. Rather, the exemplary embodiment may be readily modified in various manners depending on a design choice or any other factor without departing from the scope of the present disclosure. The drawings to be referred to in the following description of embodiments are all schematic representations. Thus, the ratio of the dimensions (including thicknesses) of respective constituent elements illustrated on the drawings does not always reflect their actual dimensional ratio.

(1) Overview

First, an overview of a display system 1 according to an exemplary embodiment will be described with reference to FIG. 1.

Figure 1:
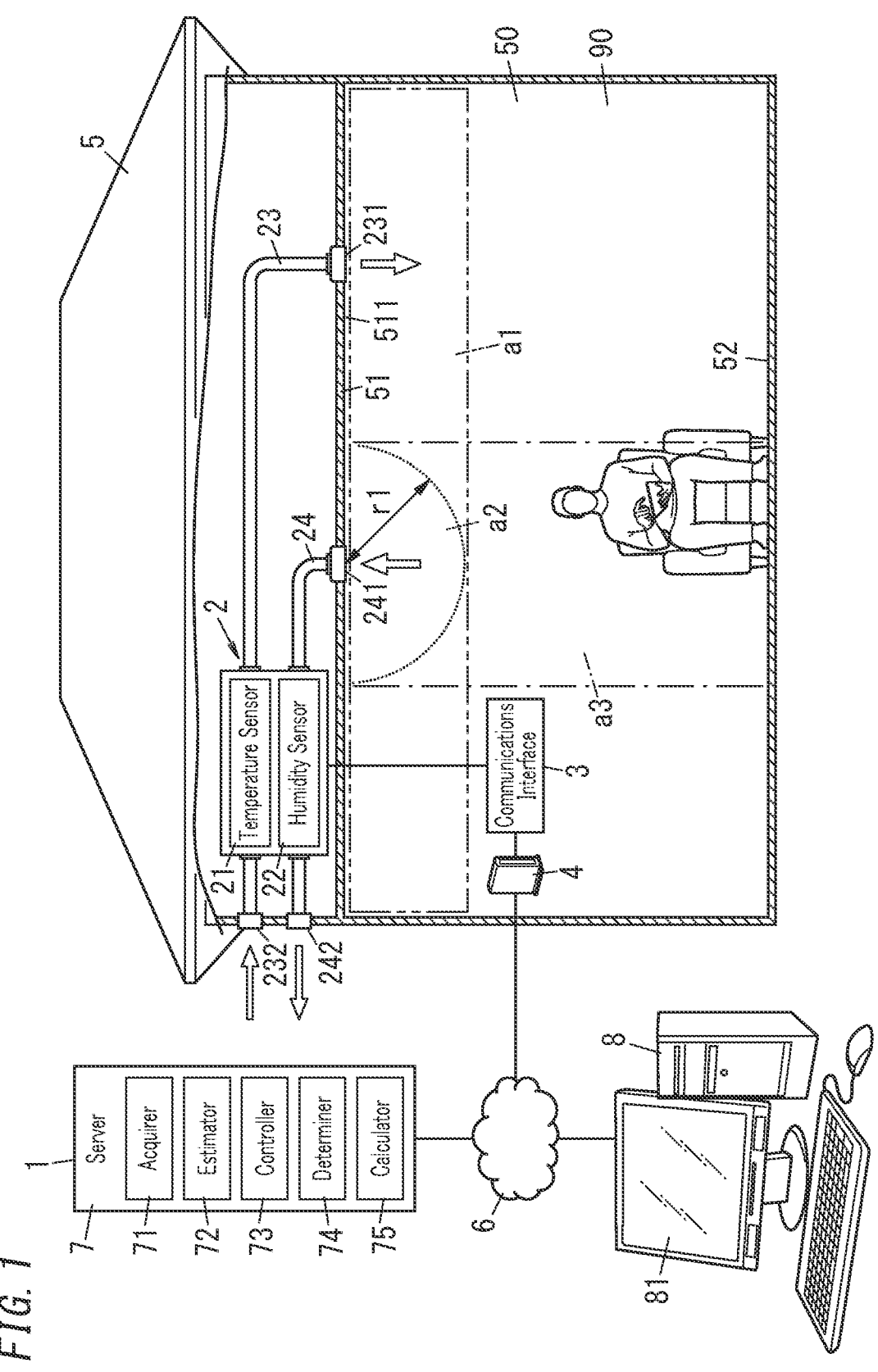
FIG. 1 is a schematic representation illustrating an overall configuration for a display system according to an exemplary embodiment.

As shown in FIG. 1, the display system 1 according to this embodiment is designed to work in cooperation with a facility 5 in which a ventilator 2 is installed.

The display system 1 according to this embodiment acquires a first detection value and a second detection value from a temperature sensor 21 and a humidity sensor 22, respectively. The temperature sensor 21 and the humidity sensor 22 are both included in the ventilator 2 installed in the facility 5. The display system 1 estimates, based on the first detection value and the second detection value, a predicted mean vote (PMV) distribution in a height direction in a room 50 of the facility 5. Then, the display system 1 makes a display device 81 of a terminal device 8 present the PMV distribution thus estimated.

(2) Details

Next, detailed configurations for the display system 1 according to this embodiment and the facility 5 and the terminal device 8 that work in cooperation with the display system 1 will be described with reference to FIGS. 1-4.

(2.1) Configuration for Facility

First, details of the facility 5 will be described with reference to FIG. 1. As used herein, examples of the "facility" include dwelling facilities for use for housing purposes and non-dwelling facilities such as stores (tenants' stores), offices, welfare facilities, educational institutions, hospitals, and factories. Examples of the non-dwelling facilities further include restaurants, amusement centers, hotels, inns, kindergartens, daycare facilities, and community centers. That is to say, the facility 5 may be a dwelling facility such as a multi-family dwelling house (i.e., a so-called "mansion" in Japan) or a non-dwelling facility such as an office building, whichever is appropriate. Alternatively, the facility 5 may also be a combination of a dwelling facility and a non-dwelling facility. For example, the facility 5 may include stores on lower floors thereof and dwelling units on upper floors thereof. In this embodiment, the facility 5 is supposed to be a single-family dwelling house as shown in FIG. 1.

As shown in FIG. 1, the facility 5 includes the ventilator 2, a communications interface 3, and a router 4.

The ventilator 2 may be, for example, a ceiling-mounted exhaust fan and performs at least one of normal ventilation or heat exchange ventilation. The ventilator 2 is provided through a ceiling 51 of a room 50 in the facility 5. The ventilator 2 according to this embodiment is an exhaust fan of class 1 ventilation and is designed to supply and exhaust the air by mechanical power. The ventilator 2 includes the temperature sensor 21, the humidity sensor 22, a supply air duct 23, and an exhaust duct 24.

The temperature sensor 21 is a sensor for detecting, as a first detection value, the temperature (spatial temperature) of the air either inside or around the ventilator 2. As used herein, the phrase "inside the ventilator 2" also refers to inside the supply air duct 23 and inside the exhaust duct 24. The temperature sensor 21 according to this embodiment is provided inside the exhaust duct 24. The temperature sensor 21 may be implemented as, for example, an infrared sensor, a thermistor, or a thermocouple. The humidity sensor 22 is a sensor for detecting, as a second detection value, the humidity (spatial humidity) of the air either inside or around the ventilator 2. The humidity sensor 22 according to this embodiment is provided inside the exhaust duct 24. The humidity sensor 22 may be implemented as, for example, an electric humidity sensor. Optionally, the temperature sensor 21 and the humidity sensor 22 may also be implemented as an integrated temperature-humidity sensor.

The supply air duct 23 is an air passage that connects the space outside the facility 5 to the indoor space of the room 50 in the facility 5 and is a duct for taking in the air outside the facility 5 and supplying the air into the room 50. The supply air duct 23 includes a first air inlet 231 arranged to face the room 50 and a second air inlet 232 provided outside the facility 5. The second air inlet 232 may be provided with, for example, a supply air fan.

The exhaust duct 24 is an air passage that connects the space outside the facility 5 to the indoor space of the room 50 in the facility 5 and is a duct for exhausting the air inside the room 50 to the outside of the facility 5. The exhaust duct 24 includes a first air outlet 241 arranged to face the room 50 and a second air outlet 242 provided outside the facility 5. The second air outlet 242 may be provided with, for example, an exhaust fan.

The communications interface 3 is connected to a network 6 such as the Internet via the router 4. The communications interface 3 transmits the first and second detection values detected by the temperature sensor 21 and the humidity sensor 22, respectively, to the display system 1 via the router 4 and the network 6. In addition, the communications interface 3 also transmits, to the display system 1, operating status information indicating whether the ventilator 2 is operating or not, i.e., whether the supply air fan and the exhaust fan of the ventilator 2 are running or not.

(2.2) Configuration for Terminal Device

Next, a configuration for the terminal device 8 will be described with reference to FIG. 1.

The terminal device 8 may be, for example, a desktop or laptop personal computer. The terminal device 8 is operated by a user such as a person living in the facility 5 or an employee of a management company that manages the facility 5. The terminal device 8 is configured to be ready to communicate with the display system 1 via the network 6.

The display device 81 may be, for example, a liquid crystal display or an organic electroluminescent (EL) display. The display device 81 presents a PMV distribution under the control of a controller 73 of a server 7 (to be described later).

(2.3) Configuration for Display System

Next, details of the display system 1 will be described with reference to FIGS. 1-4.

The display system 1 according to this embodiment is implemented as a server 7. The server 7 includes, as a major constituent element, a computer system including one or more processors and one or more memories. The server 7 performs the functions of the acquirer 71, the estimator 72, the controller 73, the determiner 74, and the calculator 75 of the server 7 shown in FIG. 1 by making the one or more processors execute a program stored in the memory. The program may be stored in advance in the memory. Alternatively, the program may also be downloaded via a telecommunications line such as the Internet or distributed after having been stored in a non-transitory storage medium such as a memory card.

The server 7 includes the acquirer 71, the estimator 72, the controller 73, the determiner 74, and the calculator 75.

The acquirer 71 acquires the first detection value and the second detection value from the communications interface 3 via the network 6. Alternatively, the acquirer 71 may also be configured to be ready to communicate with the communications interface 3 directly not via the network 6.

The estimator 72 estimates, based on the first detection value and the second detection value that are acquired by the acquirer 71, a PMV distribution representing the distribution of PMVs in a height direction in the room 50. As used herein, the "predicted mean vote (PMV)" refers to a quantitative representation indicating the degree of thermal sensations that a human being feels. The PMV is calculated based on four physical quantities (namely, room temperature, radiant temperature, relative humidity, and air speed) and two human element quantities (namely, the amount of clothing and the level of physical activity of a person present in a room). The PMV is a numerical value falling within the range from −3 to +3. The greater the magnitude of the PMV on the negative side is, the colder the human being would feel in that environment. Meanwhile, the greater the magnitude of the PMV on the positive side is, the hotter the human being would feel in that environment. The PMV, as well as its calculation method, is compliant with, for example, the ISO 07730 (third edition, Nov. 15, 2005) standard.

Figure 2:
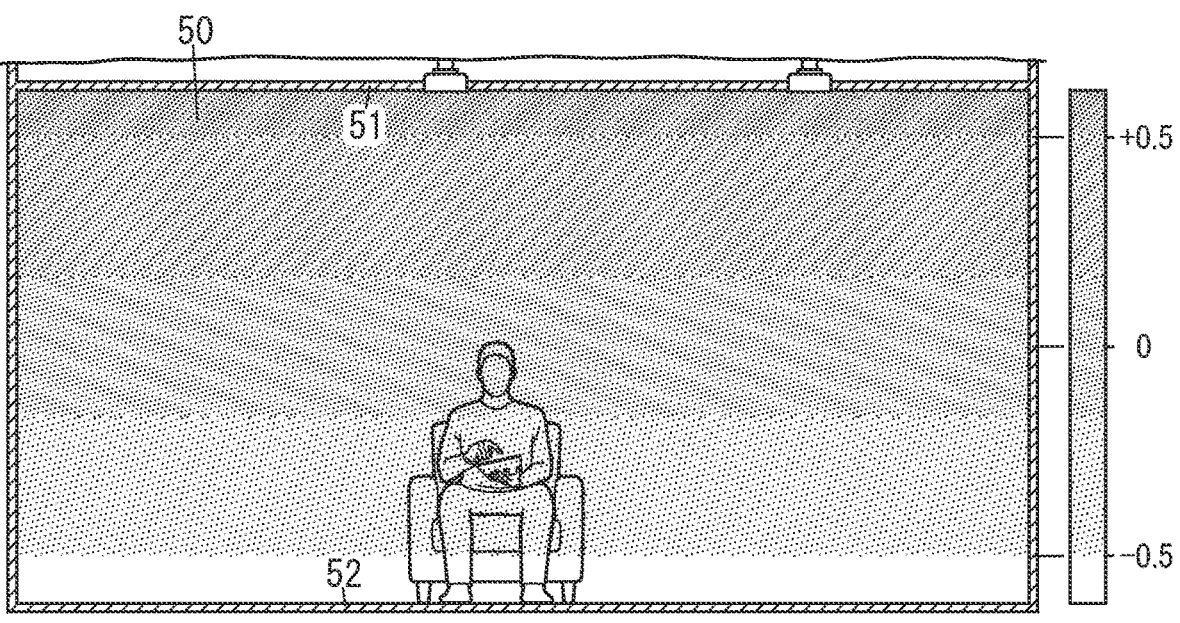
FIG. 2 schematically illustrates an indoor predicted mean vote distribution estimated by an estimator included in the display system.

The estimator 72 according to this embodiment estimates a PMV distribution in a space a3 (refer to FIG. 1) in the height direction from the ceiling 51 of the room 50 to its floor 52 (refer to FIG. 2). Note that the estimator 72 according to this embodiment estimates only a PMV distribution in the height direction and supposes the PMV distribution in a horizontal direction to be uniform. It will be described in detail in the "(3) Display method" section specifically how the estimator 72 estimates the PMV distribution.

The determiner 74 determines whether a representative value derived from the PMV distribution estimated by the estimator 72 falls outside of a preset range. In this embodiment, the preset range is a comfortable range. As used herein, the "comfortable range" refers to, for example, a PMV range that allows a human being to perform an activity comfortably. In this embodiment, the comfortable range is defined to be a range from −0.5 to +0.5. In general, if the PMV range is ±0.5, then the environment is determined to be comfortable for human beings. Also, the representative value derived from the PMV distribution refers to, for example, a maximum value, a minimum value, or an average value in the PMV distribution. Alternatively, the representative value may also be a median. The average value of the PMV distribution is calculated based on the PMV distribution and is zero in the example shown in FIG. 2.

In addition, the determiner 74 also determines whether a PMV at an arbitrary point in the height direction in the room 50 in the PMV distribution estimated by the estimator 72 falls outside of the comfortable range. The arbitrary point in the height direction may be set arbitrarily by a user such as a person living in the facility 5 or an employee of a management company of the facility 5. In this embodiment, the PMV distribution is present only in the height direction. In this embodiment, the arbitrary point in the height direction where the determiner 74 makes decision is set by a person living in the facility 5 at a height of 1.2 meters above the floor 52.

When deciding that the representative value derived from the PMV distribution or the PMV at an arbitrary point in the height direction in the room 50 fall outside of the comfortable range, the determiner 74 notifies the controller 73 to that effect.

The calculator 75 calculates the proportion of a period in which the representative value derived from the PMV distribution estimated by the estimator 72 falls within a preset comfortable range to a specified period that has been set arbitrarily. Specifically, the calculator 75 calculates the proportion of the period in which the representative value of the PMV distribution falls within the comfortable range to the specified period. In the following description, the specified period that has been set arbitrarily will be hereinafter sometimes referred to as an "evaluation period." Examples of the evaluation period include one day, one week, one month, three months, and one year. In this embodiment, the evaluation period is set by a person living in the facility 5 at one week.

In addition, the calculator 75 also calculates the proportion of a period in which the PMV at an arbitrary height in the room 50 in the PMV distribution estimated by the estimator 72 falls within the comfortable range to an arbitrary set period (evaluation period).

The calculator 75 notifies the controller 73 of the proportions thus calculated.

The controller 73 makes the display device 81 of the terminal device 8 present the PMV distribution estimated by the estimator 72. In addition, the controller 73 according to this embodiment makes, in response to the notification received from the determiner 74, the display device 81 display a notification image notifying the user that either the representative value derived from the PMV distribution or the PMV at the arbitrary point has fallen outside of the comfortable range. Furthermore, the controller 73 according to this embodiment makes the display device 81 present the proportions calculated by the calculator 75. The controller 73 according to this embodiment controls the information displayed on the terminal device 8 via the network 6.

Figure 3:
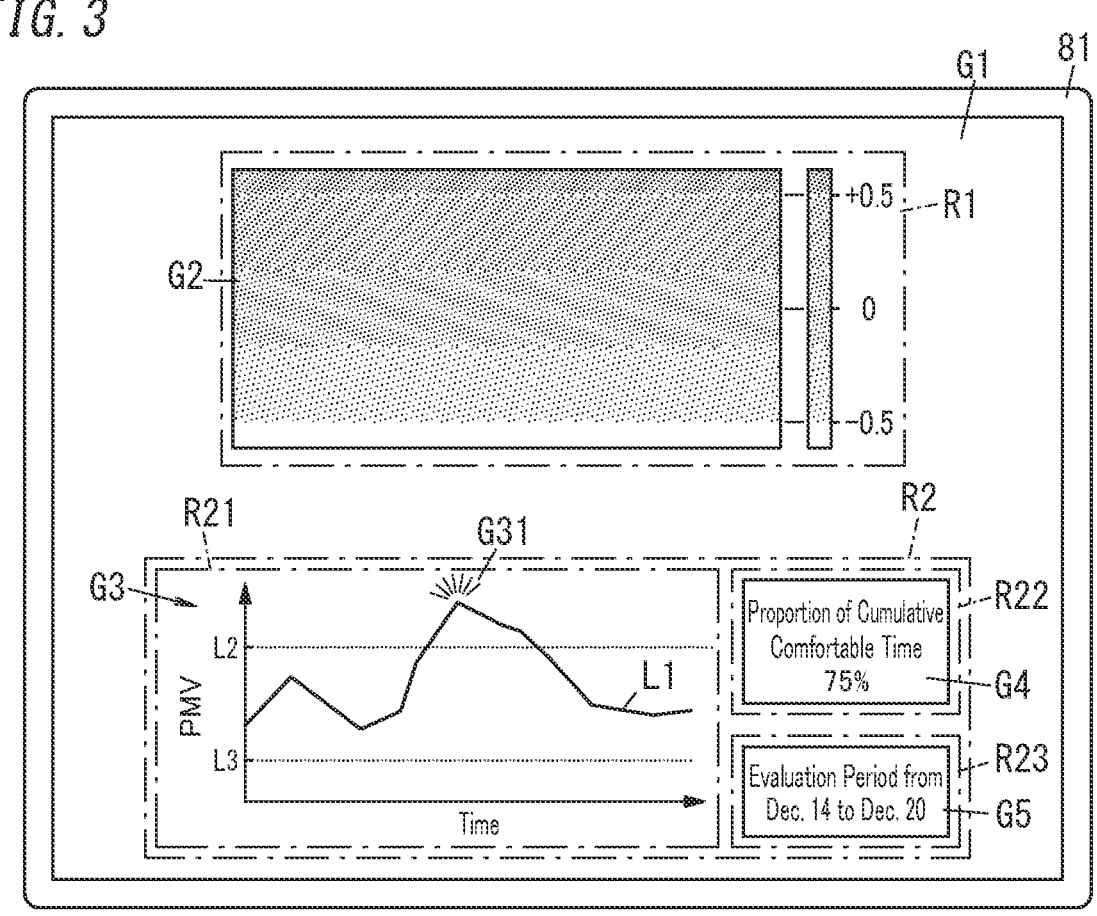
FIG. 3 schematically illustrates an on-screen image displayed on a display device provided for the display system.

FIG. 3 illustrates an exemplary on-screen image G1 displayed on the display device 81 under the control of the controller 73. In an upper region R1 of the on-screen image G1, displayed is an image G2 representing the PMV distribution in the room 50 that has been estimated by the estimator 72. The image G2 includes a PMV bar corresponding to the PMV distribution. Optionally, the image G2 representing the PMV distribution may also be superimposed on an image captured by shooting the room 50. As used herein, examples of the "image captured by shooting the room 50" include a moving picture, a still picture, and a stop-motion picture. Alternatively, the image G2 representing the PMV distribution may also be superimposed on an illustration or a CAD image, instead of an image captured by shooting the room 50.

Meanwhile, a lower region R2 of the on-screen image G1 includes regions R21, R22, and R23.

In the region R21 defined on the left-hand side of the region R2, displayed is an image G3 indicating how the PMV changes with time. In FIG. 3, the solid curve L1 indicates how the PMV at the arbitrary point in the room 50 changes with time. The numerical value L2 in FIG. 3 indicates the upper limit of the comfortable range and the numerical value L3 in FIG. 3 indicates the lower limit of the comfortable range. In the example shown in FIG. 3, an image G31 is displayed over a part, where the numerical value L2 indicating the upper limit of the comfortable range is exceeded, of the solid curve L1 indicating how the PMV changes with time. The image G31 is a notification image notifying the user that the PMV has fallen outside of the comfortable range. The image G31 is displayed to attract the user's attention to that part, where the numerical value L2 (or L3) indicating the upper limit (or lower limit) of the comfortable range is exceeded, of the solid curve L1 indicating how the PMV changes with time. Alternatively, the solid curve L1 may also indicate how the representative value (such as an average value) derived from the PMV distribution changes with time.

Figure 4:
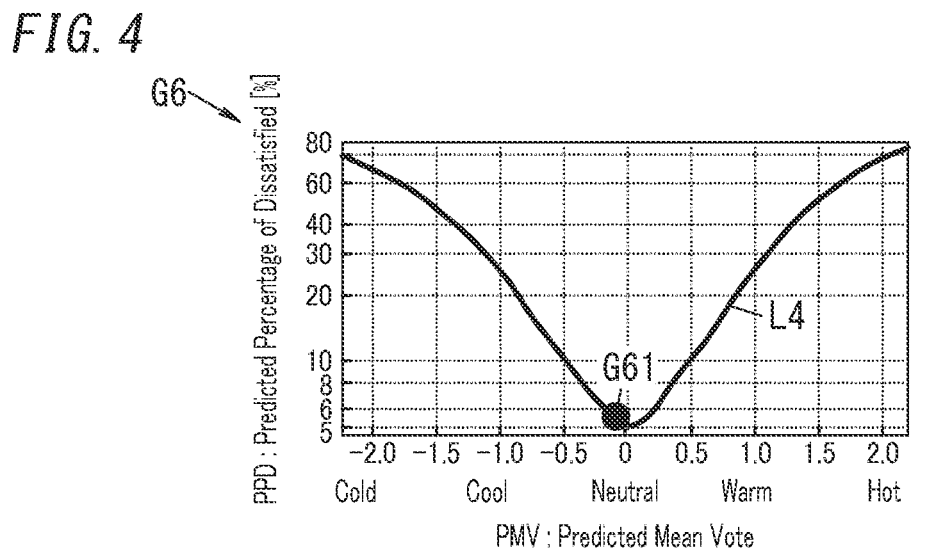

Alternatively, the controller 73 may make the display device 81 display an image G6, which is based on a PMV-PPD (predicted percentage of dissatisfied) graph as shown in FIG. 4, instead of the image G3 showing how the PMV changes with time. As used herein, the PPD is an index that establishes a quantitative prediction of the percentage of thermally dissatisfied occupants with respect to the PMV calculated (see ISO 7730). In the example shown in FIG. 4, the controller 73 indicates the current PMV by the solid circle G61 shown on the curve L4 of the PMV-PPD graph.

In the region R22 defined on the upper right part of the region R2, displayed is an image G4 indicating the proportion of the cumulative time, during which the PMV falls within the comfortable range, to the evaluation period. In this embodiment, the image G4 indicates the proportion of the cumulative time, during which the PMV falls within the comfortable range, to one week (as the evaluation period).

In the region R23 defined on the lower right part of the region R2, displayed is an image G5 indicating the beginning and end dates of the evaluation period.

(3) Display Method

Figure 5:
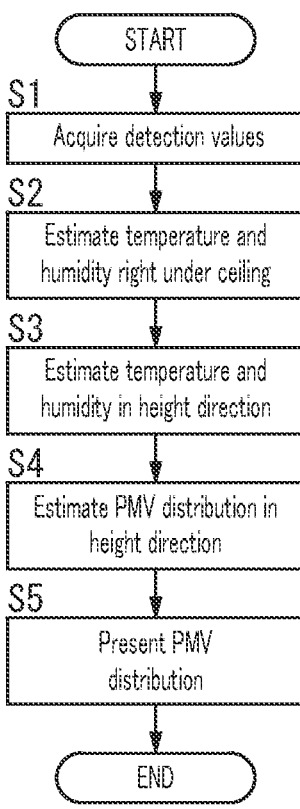
FIG. 5 is a flowchart showing the procedure of operation of the display system.

Next, a display method (i.e., how the display system 1 operates) will be described with reference to FIGS. 1-5. FIG. 5 is a flowchart showing an exemplary display method according to this embodiment.

First, the acquirer 71 of the server 7 acquires the first detection value and the second detection value from the temperature sensor 21 and the humidity sensor 22, respectively, via the network 6 (in S1 shown in FIG. 5). Next, the estimator 72 estimates, based on the first detection value acquired by the acquirer 71, a spatial temperature in the space a1 (refer to FIG. 1) on the ceiling surface 511 of the room 50 (more specifically, right under the ceiling 51). In this embodiment, the space a1 is a space located at a height of 1 meter or less under the ceiling surface 511. In addition, the estimator 72 also estimates, based on the second detection value acquired by the acquirer 71, a spatial humidity in the space a1 on the ceiling surface 511 of the room 50 (in S2 shown in FIG. 5). In this case, the position where the spatial temperature is estimated by the estimator 72 and the position where the spatial humidity is estimated by the estimator 72 are the same position. More specifically, the estimator 72 according to this embodiment estimates the spatial temperature and spatial humidity in the space a2 (refer to FIG. 1) where the straight-line distance measured from the first air outlet 241 provided through the ceiling surface 511 is equal to or shorter than r1 (refer to FIG. 1). The estimated spatial temperature calculated by the estimator 72 may be expressed by the following Equation (1) and the estimated spatial humidity calculated by the estimator 72 may be expressed by the following Equation (2):

$$Tr = \alpha 1 \times Ts + c1 \tag{1}$$

$$Hr = \alpha 2 \times Hs + c2 \tag{2}$$

In Equation(1), Tr is an estimated spatial temperature [° C.] (in the space a2), $\alpha 1$ is a coefficient, Ts is the first detection value [° C.], and c1 is a coefficient. For example, $\alpha 1$ may be 0.95 and c1 may be 0.2. In Equation (2), Hr is an estimated humidity [%] (in the space a2), $\alpha 2$ is a coefficient, Hs is the second detection value [%], and c2 is a coefficient. For example, $\alpha 2$ may be 1.05 and c2 may be 5.0.

Next, the estimator 72 estimates, by the following Equations (3) and (4), the spatial temperature and the spatial humidity on a predetermined height basis in the space a3 including the space a2 in the room 50 (in S3 shown in FIG. 5).

$$Th = \alpha 3 \times h + c3 \tag{3}$$

$$Hh = \alpha 4 \times h + c4 \tag{4}$$

In Equation (3), h is a height [m] above the floor, Th is an estimated spatial temperature at the height h [m] above the floor, $\alpha 3$ is a coefficient, and c3 is a coefficient. For example, $\alpha 3$ may be 0.5. In Equation (4), Hh is an estimated spatial humidity at the height [m] above the floor, $\alpha 4$ is a coefficient, and c4 is a coefficient. For example, $\alpha 4$ may be 0.95. Also, c3 may be expressed by the following Equation (5) and c4 may be expressed by the following Equation (6):

$$c3 = Tr - Lrf \times \alpha 3 \tag{5}$$

$$c4 = Hr - Lrf \times \alpha 4 \tag{6}$$

In Equations (3) and (4), Lrf is the height [m] of the ceiling 51. Th and Hh in the vicinity of the ceiling calculated by Equations (5) and (6), respectively, by substituting h for Lrf substantially agree with the estimated spatial temperature Tr and the estimated spatial humidity Hr, respectively.

Next, the estimator 72 estimates, based on the spatial temperature and spatial humidity that have been estimated on a height basis in the processing step S3, a PMV on a predetermined height basis in the space a3 (in S4 shown in FIG. 5). Note that the estimator 72 estimates the PMV on the supposition that the mean radiant temperature on a height basis is equal to the spatial temperature on a height basis as expressed by the following Equation (7):

$$Tmrt = Th \tag{7}$$

In this case, the estimator 72 according to this embodiment approximates the values of a metabolic rate (M) and clothing insulation (Icl) to fixed values on a season-by-season basis. One year may be divided into the four seasons, namely, summer (from June to August), winter (from December to February), spring (from March to May), and autumn (from September to November). In each of these four seasons, calculation is made with the metabolic rate and the clothing insulation supposed to be respectively fixed values. In this case, the thermal environment in spring is so similar to the thermal environment in autumn that the same values may be used both in spring and autumn. For example, the metabolic rate may be about 1.0 [W/m2] in the sitting position and about 1.2 [W/m2] in the standing position. The clothing insulation may be about 1.0 [m2·K/W] as for men's summer clothes and about 2.0 [m2·K/W] as for men's winter clothes. As for the metabolic rate and clothing insulation, see, for example, a reference entitled "Evaluation of Thermal Comfort in Houses," Housing Research Foundation Annual Report No. 23, pp. 19-32, 1996.

Also, the estimator 72 according to this embodiment supposes that the person is staying in the room and the external work (W) is zero. The estimator 72 also estimates a partial water vapor pressure (Pa) based on the spatial temperature (Th) and the spatial humidity (Hh). The indoor air speed is equal to or less than approximately 0.3 [m/s] and does not affect the PMV significantly even if the indoor air speed is supposed to be constant. Thus, the estimator 72 according to this embodiment estimates the PMV with the air speed (Var) supposed to be constant. For example, the air speed may be 0.1 [m/s].

This supposition enables calculating the PMV based on only the first and second detection values acquired from the temperature sensor 21 and the humidity sensor 22, respectively.

Next, the controller 73 makes the display device 81 (refer to FIG. 3) of the terminal device 8 (refer to FIG. 3) present the PMV distribution estimated by the estimator 72 (in S5 shown in FIG. 3).

(4) Advantages

As described above, a server 7 according to this embodiment includes an acquirer 71, an estimator 72, and a controller 73. The estimator 72 estimates, based on first and second detection values respectively provided by a temperature sensor 21 and a humidity sensor 22 both included in a ventilator 2, a predicted mean vote (PMV) distribution in a height direction in a room 50. The controller 73 makes a display device 81 of a terminal device 8 present the PMV distribution, estimated by the estimator 72, in the height direction in the room 50. This allows a user such as a person living in the facility 5 or an employee of a management company of the facility 5 to monitor the PMV easily. Then, the user such as the occupant or the employee may take an appropriate action such as changing the thermal environment according to the PMV distribution. In addition, the estimator 72 according to this embodiment may estimate the PMV distribution in the room 50 based on only the detection values provided by the temperature sensor 21 and humidity sensor 22 both included in the ventilator 2. This enables estimating the PMV in an environment surrounding the person even without using a dedicated handy measuring instrument.

Furthermore, the estimator 72 according to this embodiment estimates, based on the first detection value and the second detection value, a spatial temperature and a spatial humidity, respectively, in the space a1 on the ceiling surface 511 of the room 50. The estimator 72 estimates, based on the spatial temperature and spatial humidity thus estimated, a PMV distribution in the height direction in the room 50. The spatial temperature and spatial humidity in the space a1 are a spatial temperature and a spatial humidity in the room 50. On the other hand, the first detection value provided by the temperature sensor 21 and the second detection value provided by the humidity sensor 22 are respectively a spatial temperature and a spatial humidity in either the space inside the ventilator 2 or the space surrounding the ventilator 2. Thus, calculating the PMV distribution after the detection values have been once converted (by Equations (1) and (2)) into the spatial temperature and spatial humidity in the room 50 enables estimating the PMV distribution more accurately than in a situation where the PMV distribution in the room 50 is estimated by directly using the values provided by the temperature sensor 21 and humidity sensor 22 built in the ventilator 2.

Furthermore, the estimated temperature in the space a1 and the estimated humidity in the space a1 are estimated at an identical position by the estimator 72 according to this embodiment. Besides, the estimator 72 according to this embodiment estimates the spatial temperature and spatial humidity in the space a2 which forms part of the space a1 and where the straight-line distance from the first air outlet 241 provided through the ceiling surface 511 is equal to or shorter than r1. This improves the accuracy of the spatial temperature and spatial humidity estimated, because the air is constantly exchanged in the vicinity of the first air inlet 231 or the first air outlet 241. The estimator 72 estimates the PMV distribution based on the spatial temperature and spatial humidity in the space a2 where the straight-line distance from the first air inlet 231 or the first air outlet 241 is equal to or shorter than 1 meter, for example, thus improving the accuracy of the PMV distribution estimated.

Furthermore, the server 7 according to this embodiment further includes a determiner 74 that determines whether a representative value derived from the PMV distribution falls outside of a preset comfortable range (preset range). The controller 73 makes, when the determiner 74 decides that the representative value fall outside of the comfortable range, the display device 81 display an image G31 (notification image) notifying a user that the representative value falls outside of the comfortable range. Displaying the notification image on the display device 81 tells a user such as a person who lives in the facility 5 or an employee of a management company of the facility 5 that the representative value falls outside of the comfortable range. The representative value is any one of a maximum value in the PMV distribution, a minimum value in the PMV distribution, or an average value obtained from the PMV distribution. This increases number of indices that form criteria in determining whether the representative value derived from the PMV distribution falls outside of the comfortable range.

Furthermore, the determiner 74 according to this embodiment determines whether a PMV at an arbitrary point in the height direction in the room 50 falls outside of the comfortable range. Displaying a notification image on the display device 81 tells a user such as a person who lives in the facility 5 or an employee of a management company of the facility 5 that the PMV at the arbitrary point falls outside of the comfortable range.

Furthermore, the server 7 according to this embodiment further includes a calculator 75 that calculates the proportion of a period in which the representative value derived from the PMV distribution falls within a preset comfortable range to an arbitrarily set period (evaluation period). The controller 73 makes the display device 81 present the proportion. This allows a user such as an employee of a management company of the facility 5 to learn the proportion of a period in which the representative value falls within the comfortable range to the evaluation period. If the evaluation period is one day, for example, then the data thus collected may be used effectively as an index for preventing the onset of an acute disease such as heat stroke. On the other hand, if the evaluation period is about three months, for example, then the data thus collected may be used as data to choose the best ventilator 2 on a season-by-season basis. Furthermore, if the evaluation period is about one year, for example, then the data thus collected may be used as data to demonstrate the air conditioning capability of a property (facility 5) itself or present an advantageous feature of the property when luring a tenant.

Furthermore, the calculator 75 according to this embodiment calculates the proportion of a period in which a PMV at an arbitrary point falls within the comfortable range to the evaluation period. This allows a user such as an employee of a management company of the facility 5 to learn the proportion of a period in which the PMV at the arbitrary point falls within the comfortable range to the evaluation period.

Furthermore, the estimator 72 according to this embodiment estimates the PMV distribution in the height direction in the room 50 by the above-described Equations (1) to (7). This allows the estimator 72 according to this embodiment to estimate the PMV distribution by analysis formulae and eliminates the need for a complicated algorithm that premises the use of, for example, a cloud computing system involving machine learning, thus enabling cutting down the cost of the display system.

(Variations)

Note that the embodiment described above is only an exemplary one of various embodiments of the present disclosure and should not be construed as limiting. Rather, the exemplary embodiment may be readily modified in various manners depending on a design choice or any other factor without departing from the scope of the present disclosure.

Also, the functions of the display system 1 according to the exemplary embodiment described above may also be implemented as, for example, a display method, a (computer) program, or a non-transitory storage medium on which the program is stored. A display method according to an aspect includes an acquisition step, an estimation step, and a presentation step. The acquisition step includes acquiring a first detection value and a second detection value from a temperature sensor 21 and a humidity sensor 22, respectively. The temperature sensor 21 and the humidity sensor 22 are both included in a ventilator 2 that ventilates a room 50. The estimation step includes estimating, based on the first detection value and the second detection value that are acquired in the acquisition step, a predicted mean vote (PMV) distribution representing a distribution of predicted mean votes in a height direction in the room 50. The presentation step includes making a display device 81 present the PMV distribution estimated in the estimation step. A program according to another aspect is designed to cause one or more processors to perform the display method described above.

The display system 1 according to the present disclosure may include, for example, a computer system. The computer system may include a processor and a memory as principal hardware components thereof. The functions of the display system 1 according to the present disclosure may be performed by making the processor execute a program stored in the memory of the computer system. The program may be stored in advance in the memory of the computer system. Alternatively, the program may also be downloaded through a telecommunications line or be distributed after having been recorded in some non-transitory storage medium such as a memory card, an optical disc, or a hard disk drive, any of which is readable for the computer system. The processor of the computer system may be made up of a single or a plurality of electronic circuits including a semiconductor integrated circuit (IC) or a large-scale integrated circuit (LSI). As used herein, the "integrated circuit" such as an IC or an LSI is called by a different name depending on the degree of integration thereof. Examples of the integrated circuits include a system LSI, a very-large-scale integrated circuit (VLSI), and an ultra-large-scale integrated circuit (ULSI). Optionally, a field-programmable gate array (FPGA) to be programmed after an LSI has been fabricated or a reconfigurable logic device allowing the connections or circuit sections inside of an LSI to be reconfigured may also be adopted as the processor. Those electronic circuits may be either integrated together on a single chip or distributed on multiple chips, whichever is appropriate. Those multiple chips may be aggregated together in a single device or distributed in multiple devices without limitation. As used herein, the "computer system" includes a microcontroller including one or more processors and one or more memories. Thus, the microcontroller may also be implemented as a single or a plurality of electronic circuits including a semiconductor integrated circuit or a large-scale integrated circuit.

Next, variations of the exemplary embodiment will be enumerated one after another. Note that the variations to be described below may be adopted in combination as appropriate.

In the exemplary embodiment described above, at least some functions of the display system 1 are aggregated together in a single device (i.e., the server 7). However, this is not an essential configuration for the display system 1. Alternatively, the constituent elements of the display system 1 may also be distributed in multiple devices (housings).

For example, some functions of the display system 1 may be provided for, for example, the terminal device 8 or any device (housing) other than the server 7. Also, the display system 1 does not have to be provided outside the facility 5 (such as a single-family dwelling house) but may be provided inside the facility 5. In other words, the display system 1 may be provided in a local environment inside the facility 5. Optionally, at least some functions of the display system 1 may also be implemented as a cloud computing system, for example.

The display system 1 only needs to include at least the acquirer 71, the estimator 72, and the controller 73.

The display system 1 may include not only the server 7 but also the terminal device 8 as well.

In the exemplary embodiment described above, the display system 1 is supposed to be introduced into a single-family dwelling house as an example. However, this is only an example and should not be construed as limiting. Alternatively, the display system 1 may also be introduced into any of various other types of facilities 5 including a multi-family dwelling house (such as a so-called "mansion" in Japan) and an office.

The terminal device 8 may also be a mobile telecommunications device such as a smartphone or a tablet computer and the display device 81 may be implemented as a touch-screen panel display. The terminal device 8 does not have to be provided outside the facility 5 (such as a single-family dwelling house) but may also be provided inside the facility 5.

In the exemplary embodiment described above, the estimator 72 estimates the PMV using linear equations as Equations (1)-(7) as an example. However, this is only an example and should not be construed as limiting. Alternatively, the estimator 72 may estimate the PMV by analysis formulae other than linear equations. For example, the estimator 72 may also estimate the PMV by approximation expressions according to the indoor environment such as a high-order polynomial, a logarithmic function, or an exponential function. For example, in a facility in which both floor heating and a heater are operating, the PMV becomes relatively high around the ceiling and floor in a room. In that case, the PMV distribution may be approximated using a quadratic function, a hyperbola, or a trigonometric function, for example. If an approximation expression for estimating the PMV is an analysis formula, then an algorithm may be implemented easily. Optionally, the approximation expression for estimating the PMV may also be obtained by, for example, performing a regression analysis when the facility 5 is designed. The regression analysis may be performed based on, for example, a result of temperature and humidity simulations by air current simulation and statistic software. Alternatively, the approximation expression may also be obtained by statistical processing based on the results of environmental measurement to be performed after the facility 5 has been constructed.

In the exemplary embodiment described above, the ventilator 2 is supposed to be a ventilator of class 1 ventilation. Alternatively, the ventilator 2 may also be a ventilator of class 2 ventilation or a ventilator of class 3 ventilation. If the ventilator 2 is a ventilator of class 2 ventilation, the ventilator 2 uses mechanical power only for the purpose of supplying the air, and there is no need to provide any fan for the exhaust duct 24. On the other hand, if the ventilator 2 is a ventilator of class 3 ventilation, the ventilator 2 uses mechanical power only for the purpose of exhausting the air, and there is no need to provide any fan for the supply air duct 23.

The temperature sensor 21 and the humidity sensor 22 may also be provided inside the supply air duct 23. In that case, the estimator 72 preferably estimates, based on the first detection value and the second detection value, the spatial temperature and the spatial humidity in the space a2 where the straight-line distance from the first air inlet 231 is equal to or shorter than r1 and then estimates the PMV distribution.

The notification image does not have to be the image G31 shown in FIG. 3. Alternatively, the notification image may also be an image in which a part, falling outside of the comfortable range (i.e., the range from the numerical value L2 to the numerical value L3), of the solid curve L1 is flickered. Still alternatively, the notification image may also be an image in which the part, falling outside of the comfortable range, of the solid curve L1 is circled in red. Yet alternatively, the notification image may also be an image in which the part, falling outside of the comfortable range, of the solid curve L1 is displayed in a different color. Yet alternatively, the notification image may also be an image representing a character string notifying the user that the PMV has fallen outside of the comfortable range.

If the determiner 74 has decided that either a representative value derived from the PMV distribution or a PMV at an arbitrary point have fallen outside of the comfortable range, then the controller 73 may control a loudspeaker included in the terminal device 8, for example, to make the loudspeaker sound an alarm.

The determiner 74 may determine whether a representative value derived from the PMV distribution or a PMV at an arbitrary point falls outside of the comfortable range. If the determiner 74 has decided that the PMV have fallen outside of the comfortable range, then the controller 73 may make the display device 81 display a notification image notifying the user that the PMV has fallen outside of the comfortable range.

(Recapitulation)

As can be seen from the foregoing description, a display system (1) according to a first aspect includes an acquirer (71), an estimator (72), and a controller (73). The acquirer (71) acquires a first detection value and a second detection value from a temperature sensor (21) and a humidity sensor (22), respectively. The temperature sensor (21) and the humidity sensor (22) are both included in a ventilator (2) that ventilates a room (50). The estimator (72) estimates, based on the first detection value and the second detection value that are acquired by the acquirer (71), a predicted mean vote distribution representing a distribution of predicted mean votes in a height direction in the room (50). The controller (73) makes a display device (81) present the predicted mean vote distribution estimated by the estimator (72).

This aspect allows the display system (1) to estimate, based on first and second detection values provided respectively by a temperature sensor (21) and a humidity sensor (22) both included in a ventilator (2), a predicted mean vote distribution in a height direction in a room (50) and make a display device (81) present the predicted mean vote distribution thus estimated. This makes it easier to monitor the predicted mean vote.

In a display system (1) according to a second aspect, which may be implemented in conjunction with the first aspect, the estimator (72) estimates, based on the first detection value and the second detection value, a spatial temperature on a ceiling surface (511) of the room (50) and a spatial humidity on the ceiling surface (511) of the room (50), respectively. The estimator (72) thereby estimates, based on the spatial temperature and spatial humidity thus estimated, the predicted mean vote distribution in the height direction in the room (50).

According to this aspect, the estimator (72) estimates a spatial temperature and a spatial humidity on the ceiling surface (511) and then estimates the predicted mean vote distribution, thus improving the accuracy of the predicted mean vote distribution estimated.

In a display system (1) according to a third aspect, which may be implemented in conjunction with the second aspect, at least one of an air inlet (first air inlet 231) or an air outlet (first air outlet 241) of the ventilator (2) is provided through the ceiling surface (511). The spatial temperature and the spatial humidity are estimated by the estimator (72) at an identical position. The identical position is a position where a straight-line distance measured from either the air inlet (first air inlet 231) or the air outlet (first air outlet 241) provided through the ceiling surface (511) is equal to or shorter than a predetermined distance (straight-line distance r1).

This aspect improves the accuracy of the spatial temperature and spatial humidity estimated, because the air is constantly exchanged in the vicinity of the air inlet (first air inlet 231) or air outlet (first air outlet 241) of the ventilator (2). The estimator (72) estimates the predicted mean vote distribution based on the spatial temperature and spatial humidity at a position where the straight-line distance from either the air inlet (first air inlet 231) or air outlet (first air outlet 241) is equal to or shorter than 1 meter, for example, thus improving the accuracy of the predicted mean vote distribution estimated.

A display system (1) according to a fourth aspect, which may be implemented in conjunction with any one of the first to third aspects, further includes a determiner (74). The determiner (74) determines whether a representative value derived from the predicted mean vote distribution falls outside of a preset range. The controller (73) makes, when the determiner (74) decides that the representative value fall outside of the preset range, the display device (81) display a notification image notifying a user that the representative value falls outside of the preset range.

According to this aspect, displaying a notification image when the representative value derived from the predicted mean vote distribution falls outside of a preset range tells a user such as a person who is monitoring the display device (81) or an occupant that the representative value has fallen outside of the preset range.

In a display system (1) according to a fifth aspect, which may be implemented in conjunction with the fourth aspect, the representative value is any one of a maximum value, a minimum value, or an average value of the predicted mean vote distribution.

According to this aspect, displaying a notification image when any one of a maximum value, a minimum value, or an average value of the predicted mean vote distribution falls outside of a preset range tells a user such as a person who is monitoring the display device (81) or an occupant that the maximum value, minimum value, or average value of the predicted mean vote distribution has fallen outside of the preset range.

A display system (1) according to a sixth aspect, which may be implemented in conjunction with any one of the first to third aspects, further includes a determiner (74). The determiner (74) determines whether a predicted mean vote at an arbitrary point in the height direction in the room (50) in the predicted mean vote distribution falls outside of a preset range. The controller (73) makes, when the determiner (74) decides that the predicted mean vote at the arbitrary point fall outside of the preset range, the display device (81) display a notification image notifying a user that the predicted mean vote at the arbitrary point falls outside of the preset range.

This aspect allows a user such as a person who is monitoring the display device (81) or an occupant to learn that the predicted mean vote at the arbitrary point has fallen outside of the preset range.

A display system (1) according to a seventh aspect, which may be implemented in conjunction with any one of the first to sixth aspects, further includes a calculator (75). The calculator (75) calculates a proportion of a period in which the representative value derived from the predicted mean vote distribution falls within a preset range to an arbitrarily set period. The controller (73) makes the display device (81) present the proportion.

This aspect allows a user such as the monitoring person to learn the proportion of a period in which the representative value falls within a preset range to an arbitrarily set period. If the arbitrarily set period is one day, for example, then the data thus collected may be used effectively as an index for preventing the onset of an acute disease such as heat stroke. On the other hand, if the arbitrarily set period is about three months, for example, then the data thus collected may be used as data to choose the best ventilator (2) on a season-by-season basis. Furthermore, if the arbitrarily set period is about one year, for example, then the data thus collected may be used as data to demonstrate the air conditioning capability of a property (facility) or present an advantageous feature of the property when luring a tenant.

A display system (1) according to an eighth aspect, which may be implemented in conjunction with any one of the first to sixth aspects, further includes a calculator (75). The calculator (75) calculates a proportion of a period in which a predicted mean vote at an arbitrary point in the height direction in the room (50) in the predicted mean vote distribution falls within a preset range to an arbitrarily set period. The controller (73) makes the display device (81) present the proportion.

This aspect allows a user such as the monitoring person to learn the proportion of a period in which a predicted mean vote at an arbitrary point falls within a preset range to an arbitrarily set period. If the arbitrarily set period is one day, for example, then the data thus collected may be used effectively as an index for preventing the onset of an acute disease such as heat stroke. On the other hand, if the arbitrarily set period is about three months, for example, then the data thus collected may be used as data to choose the best ventilator (2) on a season-by-season basis. Furthermore, if the arbitrarily set period is about one year, for example, then the data thus collected may be used as data to demonstrate the air conditioning capability of a property (facility) or present an advantageous feature of the property when luring a tenant.

In a display system (1) according to a ninth aspect, which may be implemented in conjunction with any one of the first to eighth aspects, the estimator (72) estimates the predicted mean vote distribution by the following Equations (1) to (7):

$$Tr = \alpha 1 \times Ts + c1 \tag{1}$$

$$Hr = \alpha 2 \times Hs + c2 \tag{2}$$

$$Th = \alpha 3 \times h + c3 \tag{3}$$

$$Hh = \alpha 4 \times h + c4 \tag{4}$$

$$c3 = Tr - Lrf \times \alpha 3 \tag{5}$$

$$c4 = Hr - Lrf \times \alpha 4 \tag{6}$$

$$Tmrt = Th \tag{7}$$

where $\alpha 1$, $\alpha 2$, $\alpha 3$, $\alpha 4$, $c1$, $c2$, $c3$, and $c4$ are respective coefficients;
h is a height [m] above a floor;
Lrf is a height [m] of a ceiling;
V is an air speed [m/s];
Ts is the first detection value [° C.] provided by the temperature sensor;

Tr is an estimated spatial temperature [° C.] on a ceiling surface;
Th is an estimated spatial temperature [° C.] at the height h above the floor;
Tmrt is a mean radiant temperature [° C.];
Hs is the second detection value [%] provided by the humidity sensor;
Hr is an estimated humidity [%] on the ceiling surface; and
Hh is an estimated humidity [%] at the height h above the floor.

This aspect allows the estimator (72) to estimate the predicted mean vote distribution by analysis formulae and eliminates the need for a complicated algorithm that premises the use of, for example, a cloud computing system involving machine learning, thus enabling cutting down the cost.

Note that the constituent elements according to the second to ninth aspects are not essential constituent elements for the display system (1) but may be omitted as appropriate.

A display method according to a tenth aspect includes an acquisition step, an estimation step, and a presentation step. The acquisition step includes acquiring a first detection value and a second detection value from a temperature sensor (21) and a humidity sensor (22), respectively. The temperature sensor (21) and the humidity sensor (22) are both included in a ventilator (2) that ventilates a room (50). The estimation step includes estimating, based on the first detection value and the second detection value that are acquired in the acquisition step, a predicted mean vote distribution representing a distribution of predicted mean votes in a height direction in the room (50). The presentation step includes making a display device (81) present the predicted mean vote distribution thus estimated in the estimation step.

This aspect enables estimating, based on first and second detection values provided respectively by a temperature sensor (21) and a humidity sensor (22) both included in a ventilator (2), a predicted mean vote distribution in a height direction in a room (50) and making a display device (81) present the predicted mean vote distribution thus estimated. This eliminates the need to provide a lot of sensors or a dedicated sensor for the purpose of measuring the predicted mean vote distribution, thus enabling cutting down the cost.

A program according to an eleventh aspect is designed to cause one or more processors to perform the display method according to the tenth aspect.

This aspect enables estimating, based on first and second detection values provided respectively by a temperature sensor (21) and a humidity sensor (22) both included in a ventilator (2), a predicted mean vote distribution in a height direction in a room (50) and making a display device (81) present the predicted mean vote distribution thus estimated. This eliminates the need to provide a lot of sensors or a dedicated sensor for the purpose of measuring the predicted mean vote distribution, thus enabling cutting down the cost.

REFERENCE SIGNS LIST

1 Display System
2 Ventilator
21 Temperature Sensor
22 Humidity Sensor
231 First Air Inlet (Air Inlet)
241 First Air Outlet (Air Outlet)
50 Room
51 Ceiling

511 Ceiling Surface
71 Acquirer
72 Estimator
73 Controller
74 Determiner
75 Calculator
81 Display Device
G31 Image (Notification Image)
r1 Straight-Line Distance (Predetermined Distance)

The invention claimed is:

1. A display system comprising:

one or more memories; and at least one processor coupled to at least one of the one or more memories and configured to perform operations comprising:

acquiring a first detection value and a second detection value from a temperature sensor and a humidity sensor, respectively, the temperature sensor and the humidity sensor being both included in a ventilator configured to ventilate a room;

estimating, based on the first detection value and the second detection value, a predicted mean vote distribution representing a distribution of predicted mean votes in a height direction in the room; and making a display device present the predicted mean vote distribution, wherein the estimating is configured to estimate, based on the first detection value and the second detection value, a spatial temperature on a ceiling surface of the room and a spatial humidity on the ceiling surface of the room, respectively, and thereby estimate, based on the spatial temperature and spatial humidity thus estimated, the predicted mean vote distribution in the height direction in the room.

2. The display system of claim 1, wherein at least one of an air inlet or an air outlet of the ventilator is provided through the ceiling surface, the spatial temperature and the spatial humidity are estimated by estimating at an identical position, and the identical position is a position where a straight-line distance from either the air inlet or the air outlet provided through the ceiling surface is equal to or shorter than a predetermined distance.

3. The display system of claim 1, wherein the operations further comprise:

determining whether a representative value derived from the predicted mean vote distribution falls outside of a preset range, and when determining that the representative value fall outside of the preset range, making the display device display a notification image notifying a user that the representative value falls outside of the preset range.

4. The display system of claim 3, wherein the representative value is any one of a maximum value, a minimum value, or an average value of the predicted mean vote distribution.

5. The display system of claim 1, wherein the operations further comprise;

determining whether a predicted mean vote at an arbitrary point in the height direction in the room in the predicted mean vote distribution falls outside of a preset range, and when determining that the predicted mean vote at the arbitrary point fall outside of the preset range, making the display device display a notification image notifying a user that the predicted mean vote at the arbitrary point falls outside of the preset range.

6. The display system of claim 1, wherein the operations further comprise:

calculating a proportion of a period in which the representative value derived from the predicted mean vote distribution falls within a preset range to an arbitrarily set period, and making the display device present the proportion.

7. The display system of claim 1, wherein the operations further comprise:

calculating a proportion of a period in which a predicted mean vote at an arbitrary point in the height direction in the room in the predicted mean vote distribution falls within a preset range to an arbitrarily set period, and making the display device present the proportion.

8. A display system comprising:

one or more memories; and at least one processor coupled to at least one of the one or more memories and configured to perform operations comprising:

acquiring a first detection value and a second detection value from a temperature sensor and a humidity sensor, respectively, the temperature sensor and the humidity sensor being both included in a ventilator configured to ventilate a room;

estimating, based on the first detection value and the second detection value, a predicted mean vote distribution representing a distribution of predicted mean votes in a height direction in the room; and making a display device present the predicted mean vote distribution, wherein the estimating estimating the predicted mean vote distribution by the following Equations (1) to (7):

$$Tr = \alpha 1 \times Ts + c1 \qquad (1)$$

$$Hr = \alpha 2 \times Hs + c2 \qquad (2)$$

$$Th = \alpha 3 \times h + c3 \qquad (3)$$

$$Hh = \alpha 4 \times h + c4 \qquad (4)$$

$$c3 = Tr - Lrf \times \alpha 3 \qquad (5)$$

$$c4 = Hr - Lrf \times \alpha 4 \qquad (6)$$

$$Tmrt = Th \qquad (7)$$

where $\alpha 1$, $\alpha 2$, $\alpha 3$, $\alpha 4$, c1, c2, c3, and c4 are respective coefficients;

h is a height [m] above a floor;

Lrf is a height [m] of a ceiling;

V is an air speed [m/s];

Ts is the first detection value [° C.] provided by the temperature sensor;

Tr is an estimated spatial temperature [° C.] on a ceiling surface;

Th is an estimated spatial temperature [° C.] at the height h above the floor;

Tmrt is a mean radiant temperature [° C.];

Hs is the second detection value [%] provided by the humidity sensor;

Hr is an estimated humidity [%] on the ceiling surface; and

Hh is an estimated humidity [%] at the height h above the floor.

9. A display method comprising:

acquiring a first detection value and a second detection value from a temperature sensor and a humidity sensor, respectively, the temperature sensor and the humidity sensor being both included in a ventilator configured to ventilate a room;

estimating, based on the first detection value and the second detection value that are acquired in the acquisition step, a predicted mean vote distribution representing a distribution of predicted mean votes in a height direction in the room; and including making a display device present the predicted mean vote distribution, wherein the estimating is configured to estimate, based on the first detection value and the second detection value, a spatial temperature on a ceiling surface of the room and a spatial humidity on the ceiling surface of the room, respectively, and thereby estimate, based on the spatial temperature and spatial humidity thus estimated, the predicted mean vote distribution in the height direction in the room.

10. A non-transitory storage medium storing thereon a program designed to cause one or more processors to perform the display method of claim 9.

11. A display method comprising:

acquiring a first detection value and a second detection value from a temperature sensor and a humidity sensor, respectively, the temperature sensor and the humidity sensor being both included in a ventilator configured to ventilate a room;

estimating, based on the first detection value and the second detection value that are acquired in the acquisition step, a predicted mean vote distribution representing a distribution of predicted mean votes in a height direction in the room; and making a display device present the predicted mean vote distribution, wherein the estimating comprises estimating the predicted mean vote distribution by the following Equations (1) to (7):

$$Tr = \alpha 1 \times Ts + c1 \tag{1}$$

$$Hr = \alpha 2 \times Hs + c2 \tag{2}$$

$$Th = \alpha 3 \times h + c3 \tag{3}$$

$$Hh = \alpha 4 \times h + c4 \tag{4}$$

$$c3 = Tr - Lrf \times \alpha 3 \tag{5}$$

$$c4 = Hr - Lrf \times \alpha 4 \tag{6}$$

$$Tmrt = Th \tag{7}$$

where $\alpha 1$, $\alpha 2$, $\alpha 3$, $\alpha 4$, $c1$, $c2$, $c3$, and $c4$ are respective coefficients;

h is a height [m] above a floor;

Lrf is a height [m] of a ceiling;

V is an air speed [m/s];

Ts is the first detection value [° C.] provided by the temperature sensor;

Tr is an estimated spatial temperature [° C.] on a ceiling surface;

Th is an estimated spatial temperature [° C.] at the height h above the floor;

Tmrt is a mean radiant temperature [° C.];

Hs is the second detection value [%] provided by the humidity sensor;

Hr is an estimated humidity [%] on the ceiling surface; and

Hh is an estimated humidity [%] at the height h above the floor.

12. A non-transitory storage medium storing thereon a program designed to cause one or more processors to perform the display method of claim 11.

* * * * *